United States Patent [19]

Leppard et al.

[11] Patent Number: 4,584,265

[45] Date of Patent: Apr. 22, 1986

[54] COLOR-PHOTOGRAPHIC RECORDING MATERIAL

[75] Inventors: David G. Leppard, Marly; Jean Rody, Riehen, both of Switzerland

[73] Assignee: Ciba-Geigy AG, Basel, Switzerland

[21] Appl. No.: 734,233

[22] Filed: May 14, 1985

Related U.S. Application Data

[63] Continuation of Ser. No. 552,910, Nov. 17, 1983, abandoned.

[30] Foreign Application Priority Data

Nov. 18, 1982 [CH] Switzerland ........................ 6735/82

[51] Int. Cl.$^4$ ........................................ G03C 7/26

[52] U.S. Cl. .................................... 430/551; 430/216; 430/505; 430/512; 430/523; 430/961

[58] Field of Search ............... 430/505, 551, 372, 216, 430/523, 512, 961

[56] References Cited

U.S. PATENT DOCUMENTS

| | | | |
|---|---|---|---|
| 4,086,204 | 4/1978 | Cassandrini et al. | 260/45.8 NT |
| 4,108,829 | 8/1978 | Cassandrini et al. | 260/45.8 NT |
| 4,161,592 | 7/1979 | Evans et al. | 544/195 |
| 4,234,707 | 11/1980 | Rody et al. | 525/437 |
| 4,268,593 | 5/1981 | Leppard et al. | 430/551 |
| 4,294,963 | 10/1981 | Rody | 544/198 |
| 4,452,884 | 6/1984 | Leppard | 430/523 |

FOREIGN PATENT DOCUMENTS 1326889 8/1973 United Kingdom .

*Primary Examiner*—J. Travis Brown
*Attorney, Agent, or Firm*—Wenderoth, Lind & Ponack

[57] ABSTRACT s-Triazine compounds which contain in their molecule at least one sterically hindered phenol group and at least one polyalkylpiperidine group are effective optical stabilizers for photographic dyes and precursors thereof.

13 Claims, No Drawings

COLOR-PHOTOGRAPHIC RECORDING MATERIAL

This application is a continuation, of now abandoned application Ser. No. 552,210, filed Nov. 17, 1983 abandoned.

The present invention concerns a colour-photographic recording material which, in at least one light-sensitive silver halide emulsion layer and/or in at least one of the customary auxiliary layers, contains at least one specific polyalkylpiperidine compound as a stabiliser.

Polyalkylpiperidines in the form of sterically hindered amines are generally known for use as optical stabilisers for organic materials, in particular for polymers. It has also already been suggested, namely in German Offenlegungsschrift No. 2,126,954, to use polyalkylpiperidines of this type as agents against the fading of colour photographs. It has further been suggested, namely in European Patent A No. 11,051, to use, as optical stabilisers for colour photographs, certain polyalkylpiperidine derivatives which contain at least one phenol group. These polyalkylpiperidine derivatives are polyalkylpiperidine esters of hydroxybenzylmalonic acids.

In continuing this research work it was found that s-triazine derivatives which contain in their molecule at least one sterically hindered phenol group and at least one polyalkylpiperidine group have a surprisingly improved action.

Accordingly, the present invention provides a colour-photographic recording material which, in at least a light-sensitive silver halide emulsion layer, an intermediate layer, an image-receiving layer and/or a protective layer, contains, as a stabiliser, at least one s-triazine compound which contains in its molecule at least one sterically hindered phenol group and at least one polyalkylpiperidine group.

It was found that this molecular combination of sterically hindered phenol groups and polyalkylpiperidine groups with s-triazine groups has a very favourable effect on the stabilising action of the combined compounds. These stabilisers are in particular compounds of the formulae I, II or III

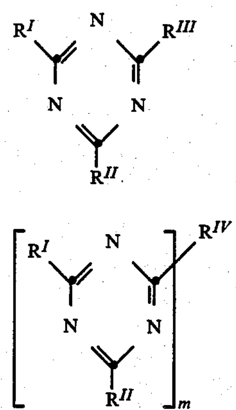

-continued

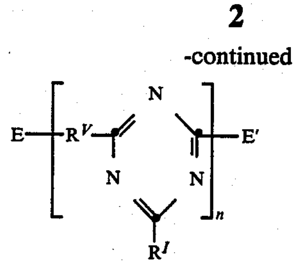

in which $R^I$, $R^{II}$ and $R^{III}$, independently of one another, are each either (a) a group of the formulae IV, V, VI or VIa

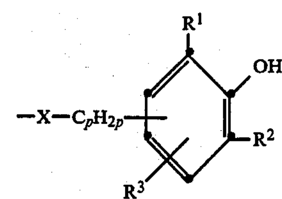

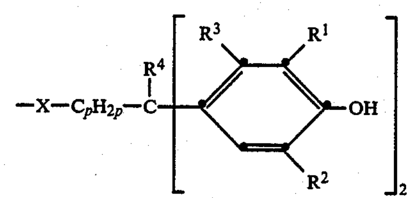

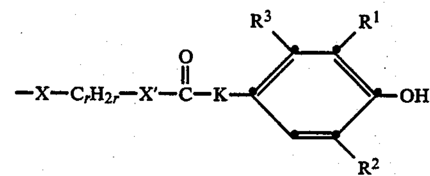

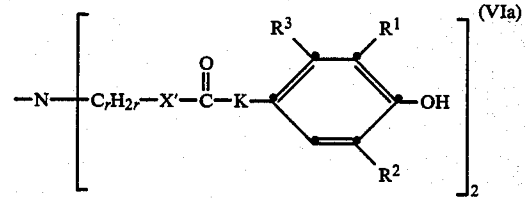

in which p is zero or a number from 1 to 12, r is an integer from 2 to 6, X is —O—, —S— or —$NR^5$—, X' is —O—, or —$NR^5$—, K is a direct bond, $C_1$–$C_6$-alkylene or a group of the formula

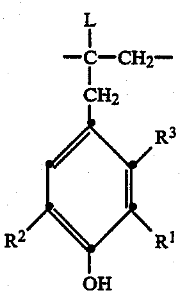

$R^1$ is hydrogen, $C_1$–$C_8$-alkyl, $C_5$–$C_8$-cycloalkyl, $C_7$–$C_9$-phenylalkyl, phenyl or $C_7$–$C_{10}$-alkylphenyl, $R^2$ is $C_1$–$C_8$-alkyl, $C_5$–$C_8$-cycloalkyl, $C_7$–$C_9$-phenylalkyl, phenyl or $C_7$–$C_{10}$-alkylphenyl, $R^3$ is hydrogen or methyl, $R^4$ is hydrogen, $C_1$-$C_{12}$-alkyl, $C_5$-$C_8$-cycloalkyl, phenyl or benzyl, $R^5$ is hydrogen, $C_1$-$C_{12}$-alkyl, $C_5$-$C_{12}$-cycloalkyl, allyl or benzyl, and L is —CN, —$COCH_3$ or —$SO_2CH_3$, or (b) a group of the formulae VII to XV (VII)

(VIII)

(IX)

(X)

(XI)

(XII)

(XIII)

(XIV)

-continued (XV)

in which Y and Y', independently of each other, are each —O— or —N($R^6$)—, $R^6$ is hydrogen, $C_1$-$C_{18}$-alkyl, $C_3$-$C_6$-alkenyl, $C_5$-$C_{12}$-cycloalkyl, $C_7$-$C_{12}$-phenylalkyl, $C_3$-$C_{12}$-alkoxyalkyl, $C_4$-$C_{12}$-dialkylaMinoalkyl, a group of the formula —$C_sH_{2s}$-C'—CO—$R^{14}$ or $-C_sH_{2s}-CO-Y''-C_pH_{2p}-$ or a group of the formula XVI (XVI)

R is hydrogen or methyl, $R^7$ is hydroxyl, $C_1$-$C_{12}$-alkyl, $C_3$-$C_6$-alkenyl, $C_3$-$C_4$-alkynyl, $C_7$-$C_{12}$-phenylalkyl, glycidyl, $C_1$-$C_4$-alkyl which is substituted by halogen, —CN, —$COOR^{15}$ or —CON($R^{16}$) ($R^{17}$), a group of the formula —CO—$R^{14}$, —CO—$OR^{15}$, —CO—N($R^{16}$) ($R^{17}$), —$CH_2$—CH($R^{18}$)—$OR^{19}$, —SO—$R^{20}$, —$SO_2$—$R^{20}$, —$OR^{15}$ or —OOC—$R^{14}$, $R^8$ is hydrogen, —CN, —$COOR^{15}$, $CONH_2$ or —CON($R^{16}$) ($R^{17}$), $R^9$ is methyl or ethyl, $R^{10}$ is hydrogen, $C_1$-$C_{12}$-alkyl, $C_5$-$C_8$-cycloalkyl or benzyl, and $R^{11}$ is $C_1$-$C_{12}$-alkyl, $C_5$-$C_8$-cycloalkyl or phenyl, or $R^{10}$ and $R^{11}$, together with the C atom to which they are bonded, are a $C_5$-$C_{12}$-cycloalkane or alkylcycloalkane ring, $R^{12}$ is hydrogen, —$OR^{21}$, —OOC—$R^{14}$ or —N($R^{22}$)—CO—$R^{14}$, and $R^{13}$ is hydrogen, —CN, —$COOR^{15}$, —$CONH_2$ or —CON($R^{16}$)($R^{17}$), or $R^{12}$ and $R^{13}$ are together a group of the formulae -continued

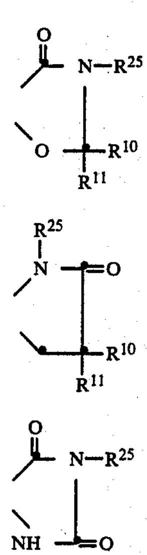

q is 1 or 2, s is an integer from 2 to 6, Y'' is —O— or —$NR^{5a}$—, in which $R^{5a}$ is defined in the same way as $R^5$ or is a group of the formula XVI, $R^{14}$ is hydrogen, $C_1$-$C_{12}$-alkyl, $C_2$-$C_6$-alkenyl, chloromethyl, $C_5$-$C_{12}$-cycloalkyl, $C_7$-$C_{12}$-phenylalkyl, phenyl, $C_7$-$C_{10}$-alkylphenyl or such phenyl, phenylmethyl or phenylethyl as is substituted by 1 or 2 $C_1$-$C_4$-alkyl groups and a hydroxyl group, $R^{15}$ is $C_1$-$C_{12}$-alkyl, allyl, benzyl or cyclohexyl, $R^{16}$ is $C_1$-$C_{12}$-alkyl, allyl, cyclohexyl, benzyl or phenyl, and $R^{17}$ is hydrogen, $C_1$-$C_8$-alkyl or allyl, or $R^{16}$ and $R^{17}$, together with the N atom, are a 5- or 6-membered heterocyclic ring, $R^{18}$ is hydrogen, $C_1$-$C_4$-alkyl, $C_2$-$C_{13}$-alkoxymethyl, phenyl or phenoxymethyl, $R^{19}$ is hydrogen, $C_1$-$C_{12}$-alkyl, —CO—$R^{14}$ or —CO—N($R^{16}$) ($R^{17}$), $R^{20}$ is $C_1$-$C_{12}$-alkyl, phenyl or $C_7$-$C_{22}$-alkylaryl, $R^{21}$ is hydrogen, $C_1$-$C_{12}$-alkyl, allyl or benzyl, $R^{22}$ is hydrogen, $C_1$-$C_{12}$-alkyl, $C_5$-$C_{12}$-cycloalkyl or benzyl, $R^{23}$ is hydrogen, methyl or ethyl, $R^{24}$ and $R^{24a}$, independently of each other, are each H or $C_1$-$C_4$-alkyl, and $R^{25}$ is hydrogen, $C_1$-$C_{12}$-alkyl, $C_3$-$C_{12}$-alkoxyalkyl, $C_5$-$C_{12}$-cycloalkyl, allyl or benzyl, or (c) a group of the formula —$OR^{26}$, —$SR^{27}$, —P(O)-$(OR^{28})_2$ or —N($R^{29}$)($R^{30}$), in which $R^{26}$ is hydrogen, $C_1$-$C_{18}$-alkyl, $C_3$-$C_6$-alkenyl, $C_3$-$C_{12}$-alkoxyalkyl, $C_4$-$C_{12}$-dialkylaminoalkyl, phenyl, $C_7$-$C_{22}$-alkylaryl, $C_7$-$C_9$-phenylalkyl or $C_5$-$C_{12}$-cycloalkyl, $R^{27}$ is $C_1$-$C_{18}$-alkyl, $C_5$-$C_{12}$-cycloalkyl, phenyl, $C_7$-$C_{12}$-alkylphenyl, $C_7$-$C_9$-phenylalkyl, —$CH_2COOR^{31}$ or —$CH_2CH_2COOR^{31}$, $R^{31}$ is hydrogen or $C_1$-$C_{12}$-alkyl, $R^{28}$ is $C_1$-$C_{12}$-alkyl, phenyl, tolyl, benzyl or a group of the formula XVI, $R^{29}$ and $R^{30}$, independently of each other, are each hydrogen, $C_1$-$C_{12}$-alkyl, $C_2$-$C_4$-alkyl which is substituted by $C_1$-$C_4$-alkoxy, $R^{14}$—COO— or $C_2$-$C_8$-dialkylamino, $C_5$-$C_{12}$-cycloalkyl, $C_3$-$C_6$-alkenyl or $C_7$-$C_9$-phenylalkyl, or $R^{29}$ and $R^{30}$, together with the N atom to which they are bonded, are a 5- or 6-membered heterocyclic ring, and $R^{III}$ can also be a group of the formula XVII

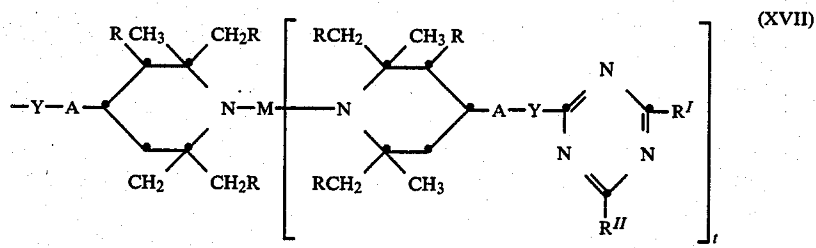

in which t is 1, 2 or 3, A is a direct bond, a —$(CH_2)_q$— group or a —Y'—$C_sH_{2s}$— group, and M, if t=1, is a divalent group, $C_2$-$C_{12}$-alkylene, $C_4$-$C_8$-alkenylene, xylylene or a radical of the formula —$CH_2$—C≡C—$CH_2$—

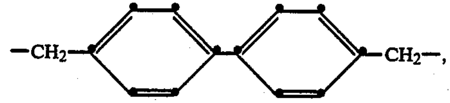

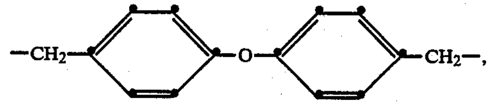

—$CH_2$—COO—B—OOC—$CH_2$—, —$CH_2$-CH(OH)—$CH_2$—, —$CH_2$CH(OH)$CH_2$—D— $CH_2$CH(OH)$CH_2$—, —$CH_2$-CH($R^{18}$)—OOC—$R^{33}$—COO—CH($R^{18}$)—$CH_2$— or —CO—NH—G—NH—CO—, in which B is $C_2$-$C_{12}$-alkylene, $C_4$-$C_8$-oxaalkylene or cyclohexylene, D is a divalent radical of the formula —O—$R^{32}$—0— or —OOC—$R^{33}$—COO—, in which $R^{32}$ is $C_2$-$C_{12}$-alkylene, $C_6$-$C_{12}$-cycloalkylene, $C_6$-$C_{12}$-arylene or —phenyl—Z—phenylene, and Z is —O—, —$HC_2$—, >C$(CH_3)_2$ or —$SO_2$, $R^{33}$ is a direct bond, $C_1$-$C_{12}$-alkylene, $C_2$-$C_6$-alkenylene, $C_6$-$C_{12}$-cycloalkylene or cycloalkenylene or $C_6$-$C_{12}$-arylene, and G is a divalent aliphatic, cycloaliphatic, aromatic or aromatic-aliphatic radical having 6-15 C atoms, M, if t=2, is a trivalent radical of the formula

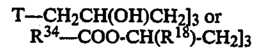

in which T is a trivalent radical of the formulae

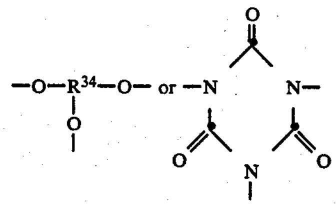

and $R^{34}$ is a trivalent aliphatic hydrocarbon radical having 3-10 carbon atoms or a trivalent aromatic hydrocarbon radical having 6-10 C atoms, and M, if t=3, is a tetravalent radical of the formula Q—$CH_2$CH(OH)$CH_2$]$_4$ or
$R^{35}$—COO-CH($R^{18}$)-$CH_2$]$_4$ in which Q is a group of the formula

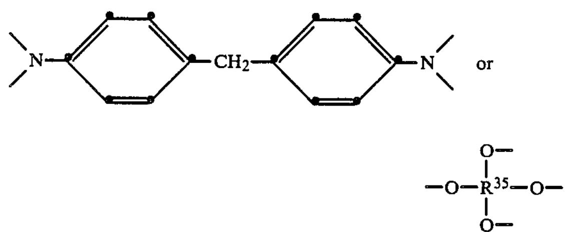

and $R^{35}$ is a tetravalent aliphatic hydrocarbon radical having 4–10 C atoms or a tetravalent aromatic hydrocarbon radical having 6–12 C atoms, $R^{IV}$ is the m-valent radical of a polyamine or of a polyol, and m is an integer from 2 to 6, $R^{V}$ is a divalent group of the formula $—Y—R^{36}—Y—$ or

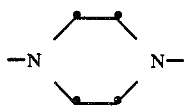

in which $R^{36}$ is $C_2$–$C_{12}$-alkylene, $C_5$–$C_{12}$-cycloalkylene, $C_8$–$C_{12}$-aralkylene, $C_6$–$C_{12}$-arylene, $C_4$–$C_8$-alkylene which is interrupted by O or $NR^5$ or a group of the formula

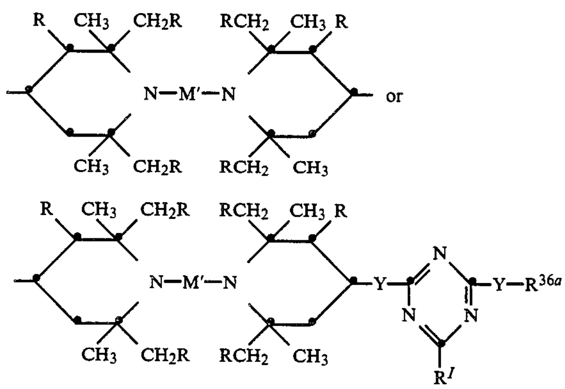

in which M' is a divalent group of the formula M, and $R^{36a}$ is $C_2$–$C_{12}$-alkylene, $C_5$-cycloalkylene, $C_8$–$C_{12}$-aralkylene, $C_6$–$C_{12}$-arylene or $C_4$–$C_8$-alkylene which is interrupted by O or $NR^5$, n is 2 to 50, and E and E' are each terminal groups, and at least one of the radicals $R^{I}$, $R^{II}$ and $R^{III}$ contains a sterically hindered phenol group and at least one of the radicals $R^{I}$, $R^{II}$, $R^{III}$, $R^{IV}$ and $R^{V}$ contains a polyalkylpiperidine radical.

In these definitions, alkyl groups $R^{18}$, $R^{24}$ or $R^{24a}$ can be, for example, methyl, ethyl, isopropyl, n-propyl, n-butyl, isobutyl or tert.-butyl. $C_1$–$C_8$-Alkyl $R^1$, $R^2$ and $R^{17}$ can furthermore also be, for example, n-amyl, isoamyl, n-hexyl, 2-ethylbutyl, isoheptyl or n-octyl. $C_1$–$C_{12}$-Alkyl $R^4$, $R^5$, $R^7$, $R^{10}$, $R^{11}$, $R^{14}$, $R^{15}$, $R^{16}$, $R^{19}$, $R^{20}$, $R^{25}$, $R^{29}$ and $R^{31}$ can furthermore also be, for example, n-decyl, isononyl or n-dodecyl. $C_1$–$C_{18}$-Alkyl $R^6$, $R^{17}$ and $R^{26}$ can furthermore also be, for example, n-tetradecyl, n-hexyldecyl or n-octadecyl.

$C_3$–$C_{12}$-Alkoxyalkyl $R^6$, $R^{25}$ and $R^{26}$ can be, for example, 2-methoxyethyl, 2-ethoxyethyl, 2-isopropoxyethyl, 3-methoxypropyl, 2-butoxyethyl, 2-butoxypropyl or 2-hexyloxyethyl. A $C_2$–$C_{13}$-alkoxymethyl $R^{18}$ can be, for example, methoxymethyl, ethoxymethyl, butoxymethyl, 2-ethylbutoxymethyl, hexyloxymethyl or dodecyloxymethyl.

$C_4$–$C_{12}$-dialkylaminoalkyl $R^6$ and $R^{26}$ can be, for example, 2-dimethylaminoethyl, 3-diethylaminopropyl, 2-dipropylaminomethyl or 3-dibutylaminopropyl.

$C_1$–$C_4$-Alkoxy-, $R^{14}COO$— or $C_2$–$C_8$-dialkylamino-substituted $C_2$–$C_4$-alkyl $R^{29}$ and $R^{30}$ can be, for example, 2-methoxyethyl, 2-butoxyethyl, 3-ethoxypropyl, 2-butoxypropyl, 2-acetoxyethyl, 2-benzoyloxypropyl, 3-lauroyloxypropyl, 2-propionyloxybutly, 2-dimethylaminoethyl, 3-diethylaminopropyl or 3-dibutylaminopropyl, $C_5$–$C_8$-Cycloalkyl $R^1$, $R^2$, $R^4$ and $R^{10}$ can be, for example, cyclopentyl, cyclohexyl, methylcyclohexyl, dimethylcyclohexyl, cycloheptyl or cyclooctyl. $C_5$–$C_{12}$-Cyclohexyl $R^5$, $R^6$, $R^{14}$, $R^{22}$, $R^{25}$, $R^{26}$, $R^{27}$, $R^{29}$ and $R^{30}$ can furthermore also be, for example, cyclodecyl or cyclododecyl.

A $C_2$–$C_6$-alkenyl $R^{14}$ can be, for example, vinyl, 2-propenyl, allyl, 2-methylvinyl, 2,2-dimethylvinyl, 3-methylallyl or 2-butylvinyl. $C_3$–$C_6$-Alkenyl $R^6$, $R^7$, $R^{26}$ and $R^{29}$ can be, for example, allyl, methallyl, 3-methylallyl or 3-dimethylallyl.

A $C_3$–$C_4$-alkynyl $R^7$ can be, for example, propargyl or 3-methylpropargyl.

A cycloalkane or alkylcycloalkane ring formed by $R^{10}$ and $R^{11}$ together with the C atom to which they are bonded can be, for example, a cyclopentane, cyclohexane, methylcyclohexane, dimethylcyclohexane, cycloheptane, cyclo- octane or cyclododecane ring.

$C_7$–$C_9$-Phenylalkyl $R^1$, $R^2$, $R^{26}$ and $R^{27}$ can be, for example, benzyl, 2-phenylethyl, 3-phenylpropyl or 1-phenylisopropyl. $C_7$–$C_{12}$-Phenylalkyl $R^6$, $R^7$, $R^{14}$, $R^{29}$ and $R^{30}$ can furthermore also be, for example 3-phenylbutyl or 6-phenylhexyl.

$C_7$–$C_{10}$-Alkylphenyl $R^1$, $R^2$ and $R^{14}$ can be, for example, tolyl, xylyl, ethylphenyl, isopropylphenyl or tert.-butylphenyl. A $C_7$–$C_{12}$-alkylphenyl $R^{27}$ can furthermore also be, for example, isoamylphenyl or n-hexylphenyl. $C_7$–$C_{22}$-Alkylaryl $R^{20}$ and $R^{26}$ can furthermore also be, for example, methylnaphthyl, butylnaphthyl, dibutylphenyl, dioctylphenyl, nonylphenyl or dodecylphenyl.

$R^{16}$ and $R^{17}$, as well as $R^{29}$ and $R^{30}$, in each case together with the N atom to which they are bonded, can be a 5- or 6-membered heterocyclic ring, which can be, for example, a pyrrolidine, piperidine, morpholine or 4-methylpiperazine ring.

$C_2$–$C_{12}$-Alkylene B, M, $R^{32}$, $R^{36}$ and $R^{36a}$ can be unbranched alkylene, for example dimethylene, trimethylene, tetramethylene, hexamethylene, octamethylene, decamethylene or dodecamethylene, or branched alkylene, for example 1,2-propylene, 1,2-butylene, 2,2-dimethyl-1,3-propylene or 2,5,5-trimethylhexamethylene. A $C_1$–$C_{12}$-alkylene $R^{33}$ can furthermore also be methylene.

A $C_4$–$C_8$-oxaalkylene B can be, for example, 3-oxapent-1,5-ylene, 4-oxahept-2,6-ylene or 3,6-dioxaoct-1,8-ylene. O- or $NR^5$-interrupted $C_4$–$C_6$-alkylene $R^{36}$ and $R^{36a}$ can furthermore also be, for example, 3-azapent-1,5-ylene, 4-azahept-2,6-ylene or 3-(methylaza)-pent-1,5-ylene.

A $C_4$–$C_8$-alkenylene M can be, for example, 2-buten-1,4-ylene, 3-hexen-1,6-ylene or 4-octen-1,8-ylene. A $C_2$–$C_6$-alkenylene $R^{33}$ can be, for example, vinylene, methylvinylene or 2-buten-1,4-ylene.

$C_6$–$C_{12}$-Cycloalkylene $R^{32}$, $R^{33}$, $R^{36}$ and $R^{36a}$ can be, for example, 1,4-cyclohexylene, 1,2-cyclohexylene, 1,4-endomethylenecyclohex-1,2-ylene, 1,4-dimethylenecyclohexane, 4,4'-dicyclohexylene or 1,4-decahydronaphthylene.

$C_6$–$C_{12}$-Arylene $R^{32}$, $R^{33}$, $R^{36}$ and $R^{36a}$ can be, for example, 1,2-phenylene, 1,3-phenylene, 1,4-naphthylene or 4,4'-diphenylene. $C_8$–$C_{12}$ Aralkylene $R^{36}$ and $R^{36a}$ can be, for example, m-xylylene, p-xylylene or 1,4-dimethylenenaphthalene.

As a divalent aliphatic, cycloaliphatic, aromatic or aromatic-aliphatic radical having 6–15 C atoms, G can be, for example, dimethylene, tetramethylene, hexamethylene, octamethylene, dodecamethylene, 2,2,4-trimethylhexamethylene, cyclohexylene, 4,4'-dicylcohexylenemethane, 1,4-phenylene, 2,4-tolylene, 1,4-naphthylene or 4,4'-diphenylmethane.

As a trivalent aliphatic radical having 3–10 C atoms, $R^{34}$ can be, for example, propane-1,2,3-triyl, 1,1,1-trimethylene-ethane or 1,1,1-trimethylenepropane.

A trivalent aromatic radical $R^{34}$ can be, for example, benzene-1,2,4-triyl or naphthalene-1,4,5-triyl.

As a tetravalent aliphatic radical having 4–10 C atoms, $R^{35}$ can be, for example 1,2,3,4-butanetetrayl or tetramethylenemethane. A tetravalent aromatic radical $R^{35}$ can be, for example, benzene-1,2,4,5-tetrayl, naphthalene-1,4,5,8-tetrayl or diphenyl-3,4,3',4'-tetrayl.

$R^{IV}$ can be the n-valent radical of a polyamine, for example the divalent radical of 1,2-diaminoethane, trimethylenediamine, tetramethylenediamine, hexamethylenediamine, octamethylenediamine, decamethylenediamine, dodecamethylenediamine, 4,4'-diaminodiphenylmethane, benzidine, 1,3-diaminobenzene, 1,4-diaminocyclohexane, 4,4'-diaminodiphenyl oxide or 1,4-di(aminoethyl)-cyclohexane, the trivalent radical of diethyltriamine or dipropylenetriamine, the tetravalent radical or triethylenetetramine or 1,5,8,12-tetraazododecane, the pentavalent radical of tetraethylenepentamine or 1,5,8,12,16-pentaazahexadecane, or the hexavalent radical of pentaethylenehexamine. As an n-valent radical of a polyol, $R^{IV}$ can be, for example, the divalent radical of ethylene glycol, 1,2-propylene glycol, 1,4-butanediol, 1,6-hexanediol, 1,8-octanediol, diethylene glycol, triethylene glycol, hydroquinone, pyrocatechol, 1,4-xylylene glycol, N-methyldiethanolamine, cyclohexane-1,4-diol, 1,4-di(hydroxymethyl)-cyclohexane or 2,2-diphenylolpropane, the trivalent radical of glycerol, trimethylolpropane, trimethylolethane or tris(4-hydroxyphenyl)-methane, the tetravalent radical of pentaerythritol or erythritol, the pentavalent radical of xylitol or arabitol, or the hexavalent radical of dipentaerythritol.

Preferred stabilisers are those compounds of the formula, I, II or III which contain in their molecule at least one sterically hindered phenol group and at least one N-substituted 2,2,6,6-tetramethylpiperidine group.

In preferred stabilisers of the formula I, $R^{I}$, $R^{II}$ and $R^{III}$ are each (a) a group of the formula IVa

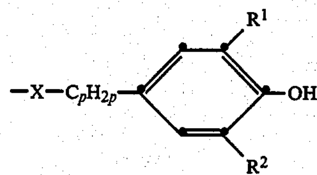

(IVa)

in which p is an integer from 1 to 4, and X, $R^1$ and $R^2$ are as defined above, (b) a group of the formulae VIIa or XVa

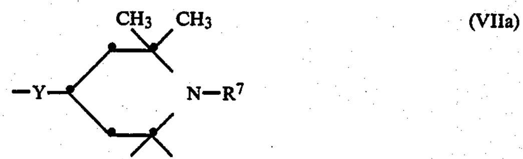

(VIIa)

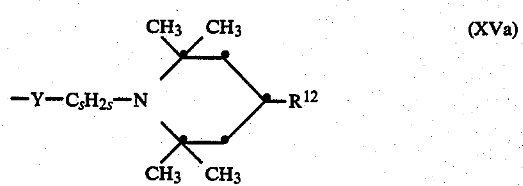

(XVa)

in which Y is —O— or —$NR^6$—, and $R^6$, $R^7$, $R^{12}$ and s are as defined above, or (c) a group of the formula —$OR^{26}$, —$SR^{27}$, —P(O)-$(OR^{28})_2$ or —$N(R^{29})(R^{30})$, in which $R^{26}$, $R^{27}$, $R^{28}$, $R^{29}$ and $R^{30}$ are as defined above, and at least one of the radicals $R^{I}$, $R^{II}$ and $R^{III}$ contains a sterically hindered phenol group, and at least one of the radicals $R^{I}$, $R^{II}$ and $R^{III}$ contains an N-substituted 2,2,6,6-tetramethylpiperidine group.

In particularly preferred stabilisers of the formula I, $R^{I}$, $R^{II}$ and $R^{III}$, independently of one another, are each (a) a group of the formula IVa in which $R^1$ is hydrogen or $C_1$–$C_4$-alkyl, $R^2$ is $C_1$–$C_4$-alkyl, and X and p are as defined above, or (b) a group of the formula VIIa or XVa in which Y is —O— or —$NR^6$—, $R^6$ is hydrogen, $C_1$–$C_8$-alkyl, allyl, cyclohexyl, benzyl or a group of the formula —$C_sH_{2s}$—X'—CO—$R^{14}$ in which s=2 or 3, X' is —O— and $R^{14}$ is such phenyl, phenylmethyl or phenylethyl as is substituted by 1 or 2 $C_1$–$C_4$-alkyl groups and a hydroxyl group, $R^7$ is methyl, allyl, benzyl, 2-hydroxyethyl, acetyl, acryloyl or a group of the formula —$CON(R^{16})(R^{4/7})$ in which $R^{16}$ is $C_1$–$C_8$-alkyl, cyclohexyl or phenyl, and $R^{17}$ is hydrogen or $C_1$–$C_8$-alkyl, and $R^{12}$ is hydrogen, or (c) a group of the formula —$OR^{26}$, —$SR^{27}$ or —$N(R^{29})(R^{30})$ in which $R^{26}$ is $C_1$–$C_{12}$-alkyl, phenyl, $C_7$–$C_{22}$-alkylaryl, benzyl or cyclohexyl, $R^{27}$ is $C_1$–$C_{12}$-alkyl, cyclohexyl, phenyl, —$CH_2COO$($C_1$–$C_{12}$-alkyl) or —$CH_2CH_2COO$($C_1$–$C_{12}$-alkyl), and $R^{29}$ and $R^{30}$ are each hydrogen, $C_1$–$C_{12}$-alkyl, benzyl or allyl.

In preferred stabilisers of the formula II, those are preferred, in which m=2 and $R^{IV}$ is a divalent group of the formula —$N(R^6)$—$R^{37}$—$N(R^6)$— or —N 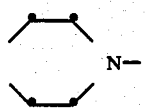 N— in which $R^{37}$ is $C_2$–$C_{12}$-alkylene, $C_4$–$C_8$-alkylene which is interrupted by —O— or —$NR^5$—, $C_6$–$C_{15}$-arylene, $C_8$–$C_{12}$-aralkylene or $C_5$–$C_{12}$-cycloalkylene, and $R^5$ and $R^6$ are as defined above, or m=3 and $R^{IV}$ is a trivalent group of the formula

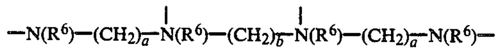

or $m=4$ and $R^{IV}$ is a tetravalent group of the formula $$-N(R^6)-(CH_2)_a-N(R^6)-(CH_2)_b-N(R^6)-(CH_2)_a-N(R^6)-$$

in which a is 2 or 3, b is 2-12 and $R^6$ is as defined above.

In preferred stabilisers of the formula III, $R^V$ is a divalent group of the formula $-N(R^6)-R^{36a}-N(R^6)-$ in which $R^{36a}$ and $R^6$ are as defined above.

In particularly preferred stabilisers of the formula III, the terminal group E is predominantly hydrogen, and the terminal group E' is predominantly a group of the formula $-N(R^6)-R^{36a}-NHR^6$.

In further particularly preferred stabilisers of the formula III, $R^I$ is a group of the formula

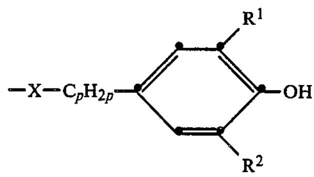

and $R^V$ is a group of the formula

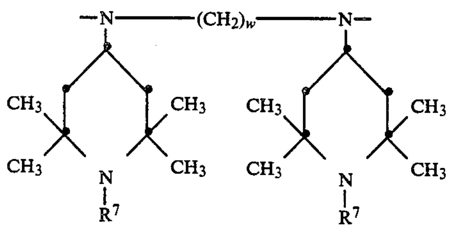

in which w is 2-6 and $R^1$, $R^2$, X, p and $R^7$ are as defined above, in particular in which p is 1-4, X is —O—, —S—, —NH— or —N($C_1$-$C_4$-alkyl)—, $R^1$ is hydrogen or $C_1$-$C_4$-alkyl, $R^2$ is $C_1$-$C_4$-alkyl, w is 2-6, and $R^7$ is methyl, allyl, benzyl, 2-hydroxyethyl, acetyl, acryloyl or a group of the formula $-CON(R^{16})(R^{17})$ in which $R^{16}$ is $C_1$-$C_8$-alkyl, cyclohexyl or phenyl and $R^{17}$ is hydrogen or $C_1$-$C_8$-alkyl.

The compounds of the formula I are known from U.S. Pat. 4,161,592 or can be prepared analogously thereto, namely by stepwise reaction of cyanuric chloride with the corresponding compounds $R^IH$, $R^{II}H$ and $R^{III}H$.

If $R^{III}$ is a group of the formula XVII, the compounds can be prepared by reacting the corresponding compounds of the formula I in which $R^{III}$ is a group of the formula

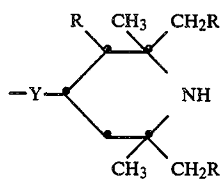

with a dihalide, with epichlorohydrin or with a diepoxide, triepoxide or tetraepoxide as described in U.S. Pat. No. 4,294,963 or with a diisocyanate of the formula OCN-G-NCO as described in Swiss Patent Application No. 9524/82.

The compounds of the formula II can be prepared analogously to U.S. Pat. No. 4,108,829 by stepwise reaction of cyanuric chloride with the monofunctional compounds $R^IH$ and $R^{II}H$ and with a polyamine $R^{IV}(H)_m$.

The compounds of the formula III are polymers or oligomers and can be prepared analogously to U.S. Pat. No. 4,086,204, by stepwise reaction of cyanuric chloride with a monofunctional compound $R^IH$ and with a difunctional compound $H-R^V-H$, in which the terminal group E can be H or a group of the formula

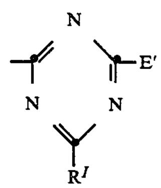

and the terminal group E' can be Cl or a $-R^V-H$ group.

The nature of the terminal groups can be controlled in such a way by using an excess of one or the other polycondensation component that one terminal group is predominantly present at both ends of the molecule. In addition, the terminal groups can be modified by chemical reactions, as described in U.S. Pat. No. 4,234,707. For example, terminal chlorotriazine groups can be converted into terminal hydroxytriazine groups by hydrolysis.

The degree of polycondensation n is a number average which can range from 2 to 50. The polycondensate is always a mixture of products of different molecular weights. The products preferably have an average degree of polycondensation n=2-10. This restriction of the molecular weight can be obtained in a manner known per se by using one of the two components in excess or by adding a monofunctional compound as a chain terminator.

Specific examples of stabilisers of the formula I are the compounds of the following formulae:

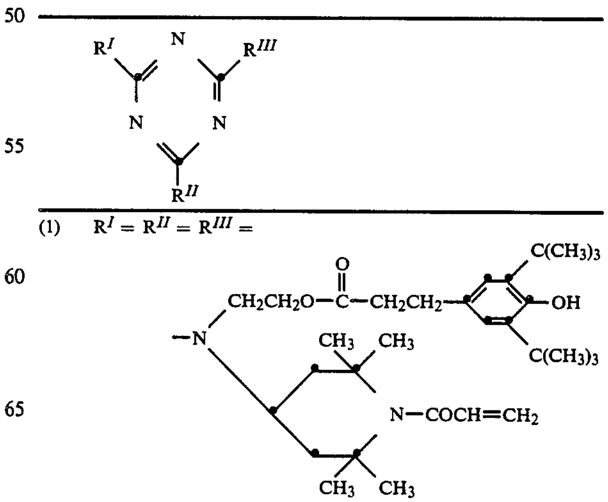

(1) $R^I = R^{II} = R^{III} =$

-continued
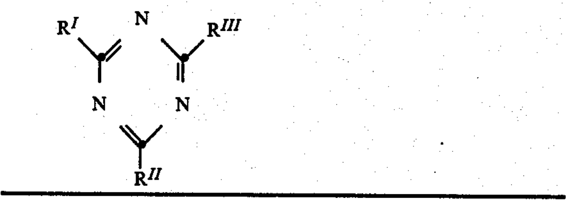
(2) $R^{I} = R^{II} = R^{III} =$
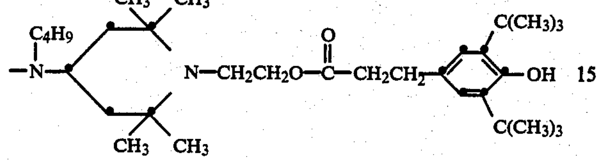
(3)
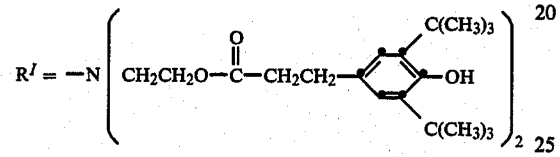
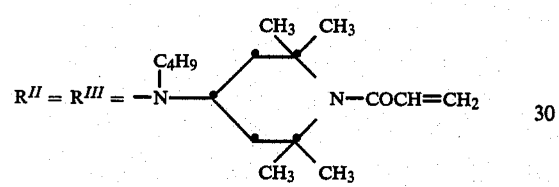
(4)
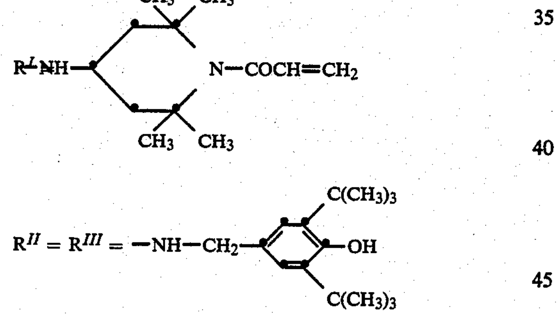
(5)
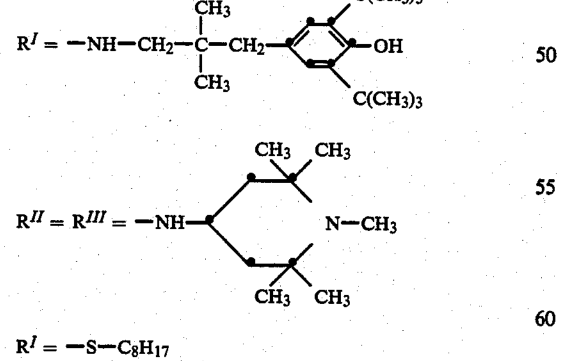
(6) $R^{I} = -S-C_8H_{17}$
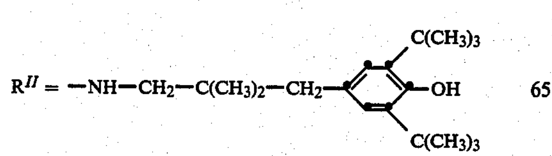
-continued
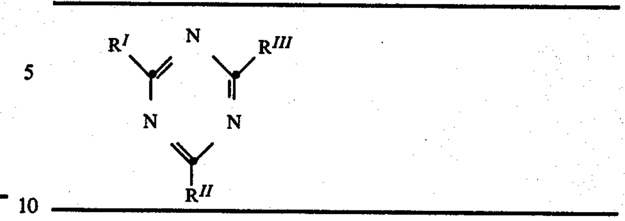
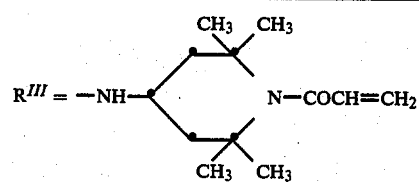
(7) $R^{I} = -P(O)(OC_2H_5)_2$
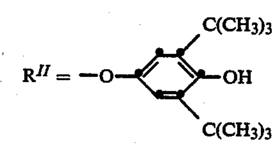
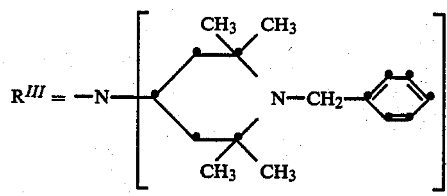
(8)
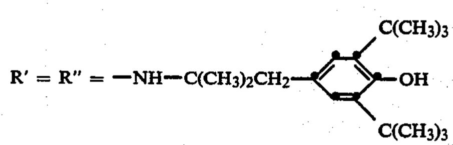
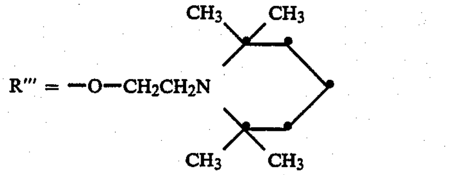
(9)
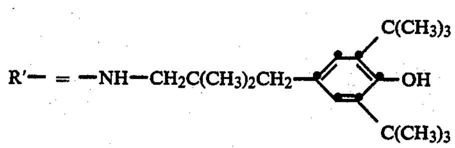
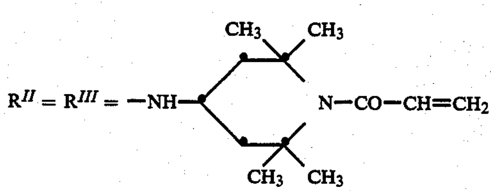
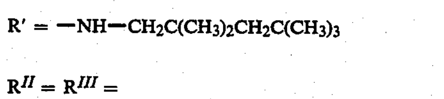
(10) $R' = -NH-CH_2C(CH_3)_2CH_2C(CH_3)_3$
$R^{II} = R^{III} =$ -continued
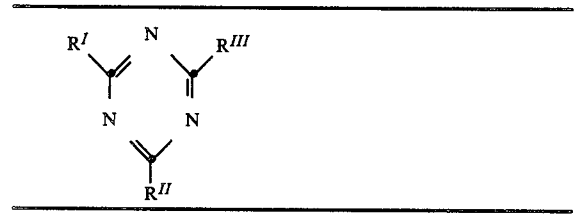
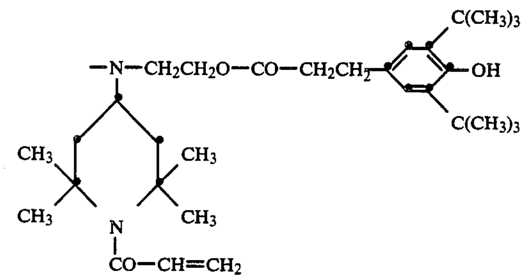
(11) R' =
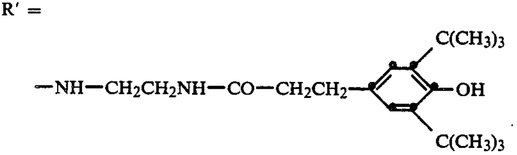
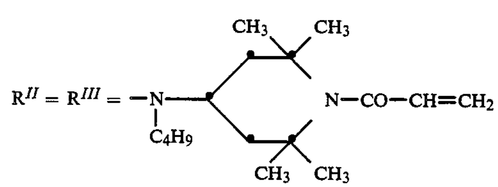
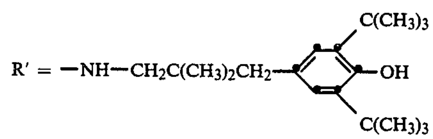
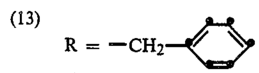
(12) R = CO—CH=CH₂
(13)
(14)
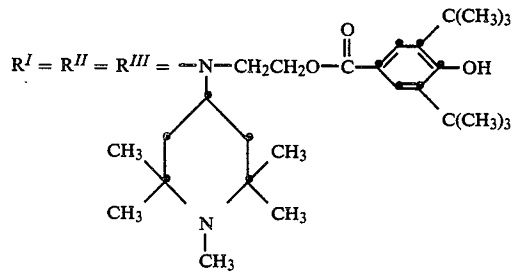
(15) $R^I = R^{II} = R^{III} =$
-continued
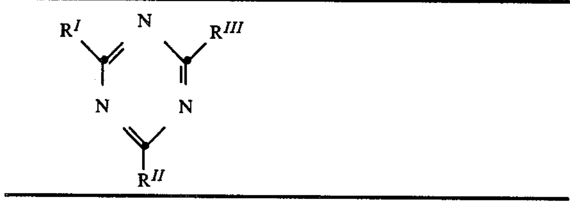
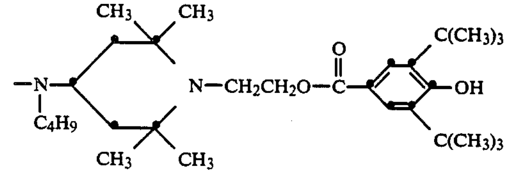
Examples of stabilisers of the formula II are the following compounds:
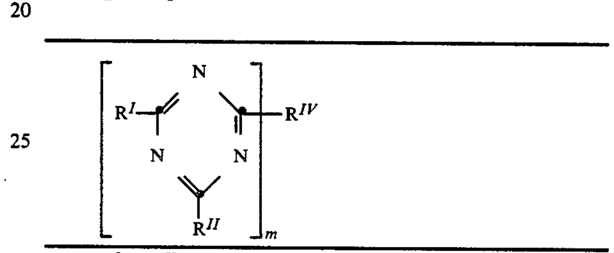
(16) $R^I = R^{II} =$
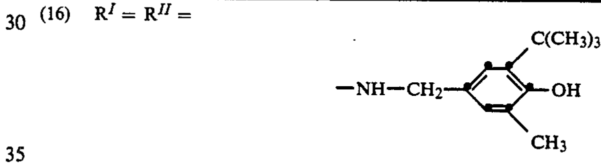
m = 2
$R^{IV} =$
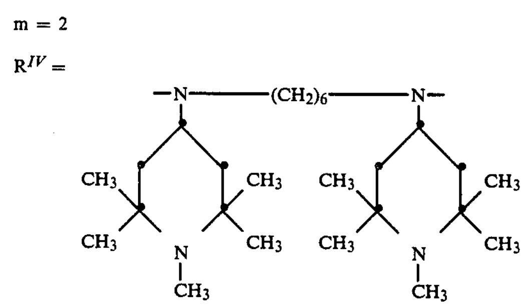
(17) $R^I =$
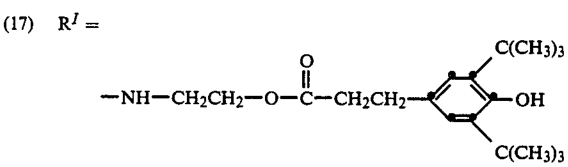
$R^{II} =$
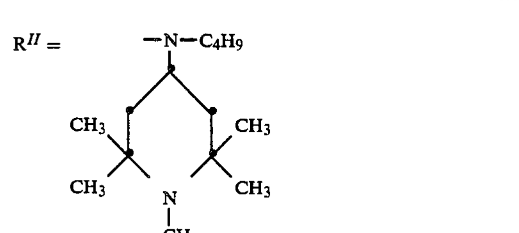
m = 3
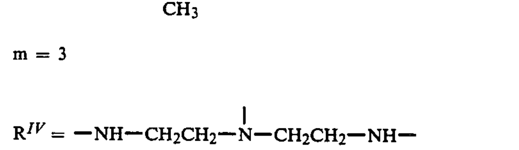

-continued

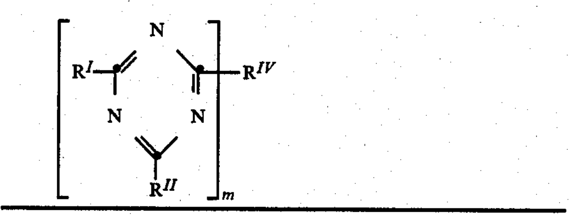

(18) $R^I = R^{II} =$

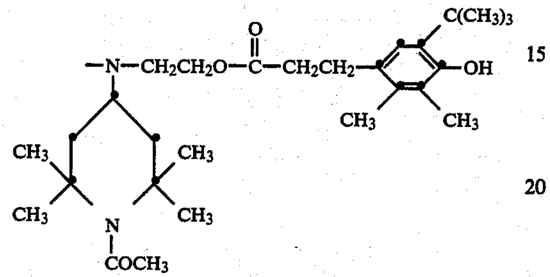

m = 4

$R^{IV} = -NH-(CH_2)_3-N-(CH_2)_6-N-(CH_2)_3-NH-$

Examples of compounds of the formula III are the following compounds:

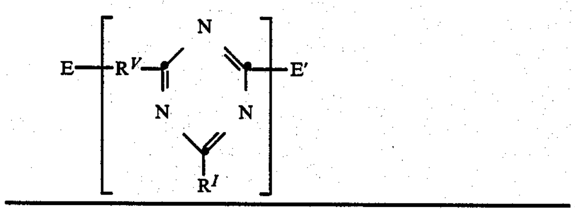

(19)

$R^I =$

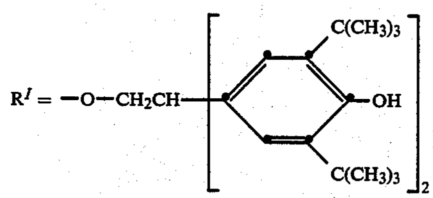

$R^V =$

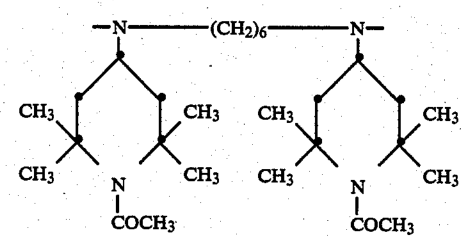

(20) $R^I =$

-continued

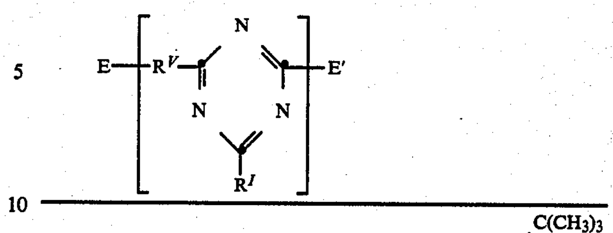

$R^V = -NH-(CH_2)_3-N(CH_3)-(CH_2)_3-NH-$

The stabilisers of the formula I, II and III can be incorporated into a photographic material in a known manner, either alone or together with other compounds.

In general, the stabilisers, alone or together with other compounds, in particular with the colour couplers, are incorporated into the photographic material in the form of a dispersion which contains no solvent, a high- or low- boiling solvent or a mixture of such solvents. A further suitable way of incorporating the stabilisers is to incorporate them into the photographic material together with a polymer in the form of a latex, alone or together with further compounds.

The dispersions are then used to prepare the layers of colour-photographic recording materials. These layers can be, for example, intermediate or protective layers, but in particular light-sensitive (blue-, green- and red-sensitive) silver halide emulsion layers in which, in the course of developing the exposed recording material, the bluish green (cyan), purple (magenta) and yellow dyes are formed from the corresponding colour couplers.

The silver halide layers can contain any colour couplers, in particular bluish green, purple and yellow couplers, which are used to form said dyes and hence the colour pictures.

Since the substrate has an effect on the action and stability of the stabilisers, it is preferable to use substrates (solvents, polymers) which, together with the stabilisers, make the materials to be stabilised as stable as possible.

In general the stabilisers are incorporated into layers which additionally contain a silver halide dispersion prepared and sensitised by customary methods. However, they can also be present in layers adjacent to layers containing silver halide.

The photographic materials according to the invention have a conventional structure and components which enhance, or at least do not adversely affect, the effectiveness of the stabilisers.

In the photographic recording material according to the present invention, the stabilisers of the formula I, II and III can be combined in the same layer not only with the colour couplers but also, in addition, with ultraviolet absorbers or other optical stabilisers.

If the diffusion transfer method is used the stabiliser can also be incorporated into a receiving layer.

The colour-photographic materials according to the invention can be processed in a customary manner. Furthermore, in the course of or after the processing they can be treated in a manner which further increases their stability, for example by treating them in a stabiliser bath or by applying a protective coating.

In certain cases the stabilisers to be used according to the invention are also suitable for protecting colour-photographic layers in which the dyes are directly incorporated into the emulsion and the image is generated by selective bleaching.

The amount of stabiliser(s) can vary within wide limits and is, for example, within the range from 1 to 2,000 mg, preferably 100 to 800 and in particular 200–500 mg per $m^2$ of the layer into which it or they is or are incorporated.

If the photographic material contains one or more UV absorbers, it or they can present in one layer together with the stabiliser or in an adjacent layer. The amount of UV absorber can vary within the wide limits and is, for example, within the range from 200 to 2,000 mg, preferably 400 to 1,000 mg, per $m^2$ of the layer. Examples of suitable UV absorbers are those of the benzophenone, acrylonitrile, thiazolidone, benzotriazole, oxazole, thiazole and imidazole type.

The colour pictures obtained with recording material according to the invention by exposure to light and developing have very good light fastness to visible and ultraviolet light. The compounds of the formula I, II and III are virtually colourless, so that they do not discolour the pictures; moreover, they are highly compatible with the customary photographic additives present in the individual layers. Because they are so highly effective they can be used in a low amount, and in this way they are prevented from precipitating or crystallising out when they are incorporated in the form of an organic solution into the aqueous binder emulsions which are used for preparing photographic layers. The stabilisers of the formula I, II and III have no adverse effect on the individual process steps necessary after exposure of the photographic recording material to obtain the colour pictures. Furthermore, the so-called pressure fogging, which frequently arises in the case of blue-sensitive emulsions, can be largely suppressed. Pressure fogging can arise, for example, when photographic materials (silver halide emulsion layers which are present on a support of natural or synthetic materials) are subjected to mechanical stresses, for example twisting, bending or rubbing, in the course of the preparation or in the course of the treatment before the development (T. H. James, The Theory of Photographic Process, 4th edition, Macmillan, New York, N.Y. 1977, page 23 et seq., page 166 et seq.).

EXAMPLE 0.087 of the yellow coupler of the formula

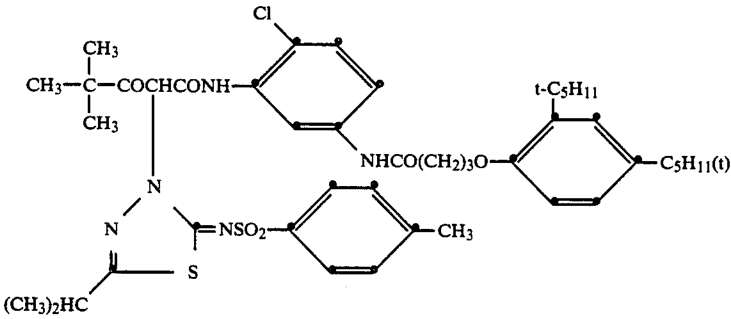

and 0.026 g of one of the stabilizrs given in the table below are dissolved in 2.0 ml of a mixture of tricresyl phosphate/ethyl acetate (1.5 g in 100 ml). To this solution are added 7.0 ml of a 6% gelatin solution, 0.5 ml of an 8% solution of the wetting agent of the formula

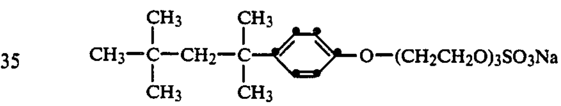

in isopropanol/water (3:4) and 0.5 ml of water, and the mixture is emulsified using ultrasound of 100 watt power for 5 minutes.

2.5 ml of the emulsion thus obtained has added to it 2.0 ml of a silver bromide emulsion containing 6.0 g of silver per liter, 0.7 ml of a 1% aqueous solution of the curing agent of the formula

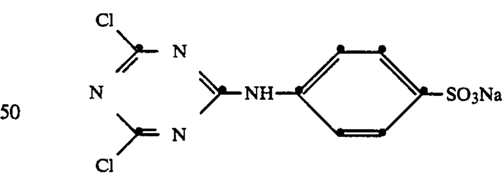

and 3.8 ml of water, and the mixture is brought to pH 6.5 and is poured onto white subbed plastic-coated paper drawn over a glass plate.

When the film has solidified it is dried at room temperature in a drying cabinet using circulating air.

7 days later, samples cut to a size of 35×180 mm are exposed under a step wedge to 3,000 Lux's and are then processed in Kodak's Ektaprint® 2 process.

The yellow weges thus obtained are irradiated in an Atlas Weather-Ometer using a 2,500 w xenon lamp to a total of 42 kjoule/$cm^2$ (a comparative sample contains no optical stabiliser). The resulting colour density loss is determined by measuring the colour density at $\lambda_{max}$ using a densitometer (TR 924 A supplied by Macbeth).

The results are given in the following table.

| Stabiliser compound No. | Percentage colour density loss |
|---|---|
| 1 | 22 |
| 2 | 19 |
| 8 | 23 |
| 9 | 23 |
| 10 | 22 |
| without stabiliser | 36 |

What is claimed is:

1. A colour-photographic recording material which, in at least a light-sensitive silver halide emulsion layer, an intermediate layer, an image-receiving layer/and or a protective layer, contains, as a stabiliser, a light stabilizing amount of at least one s-triazone compound which contains in its molecule at least one sterically hindered phenol group and at least one polyalkylpiperidine group.

2. A colour-photographic recording material according to claim 1, which contains, as a stabiliser, a compound of the formulae I, II or III

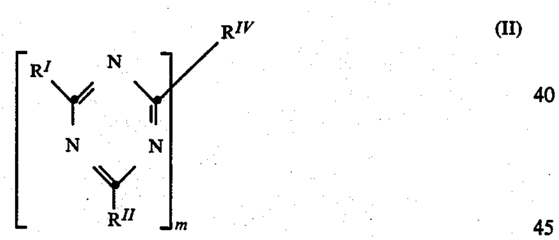

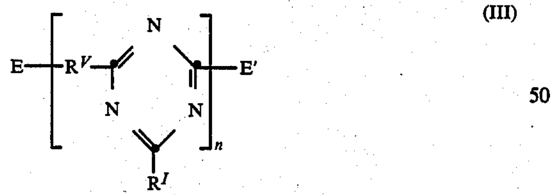

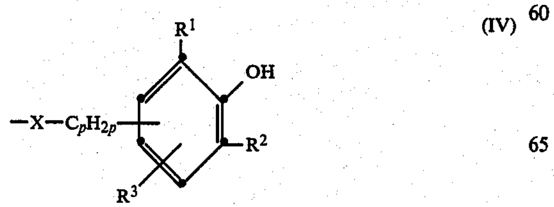

in which $R^I$, $R^{II}$ and $R^{III}$, independently of one another, are each either (a) a group of the formulae IV, V, VI or VIa -continued

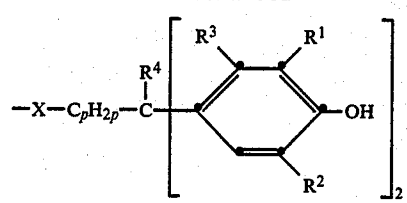

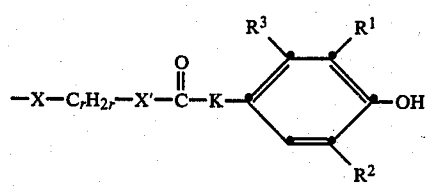

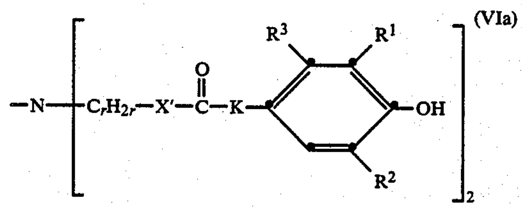

in which p is zero or an integer of from 1-12, r is an integer from 2-6, X is —O—, —S— or —$NR^5$—, X' is —O— or —$NR^5$—, K is a direct bond, $C_1$-$C_6$-alkylene or a group of the formula

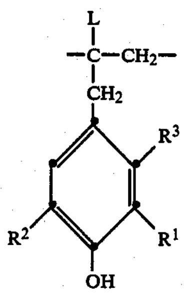

$R^1$ is hydrogen, $C_1$-$C_8$-alkyl, $C_5$-$C_8$-cycloalkyl, $C_7$-$C_9$-phenylalkyl, phenyl or $C_7$-$C_{10}$-alkylphenyl, $R^2$ is $C_1$-$C_8$-alkyl, $C_5$-$C_8$-cycloalkyl, $C_7$-$C_9$-phenylalkyl, phenyl or $C_7$-$C_{10}$-alkylphenyl, $R^3$ is hydrogen or methyl, $R^4$ is hydrogen, $C_1$-$C_{12}$-alkyl, $C_5$-$C_8$-cycloalkyl, phenyl or benzyl, $R^5$ is hydrogen, $C_1$-$C_{12}$-alkyl, $C_1$-$C_{12}$-cycloalkyl, allyl or benzyl, and L is —CN, —$COCH_3$ or —$SO_2CH_3$, or (b) a group of the formulae VII to XV

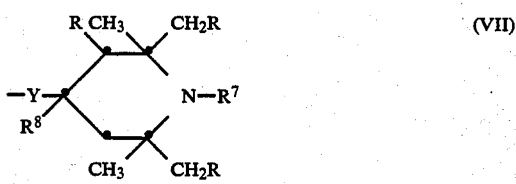

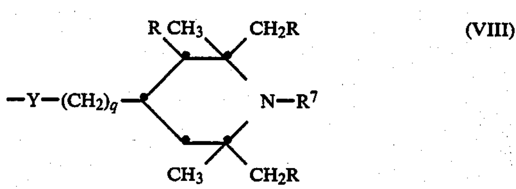

-continued

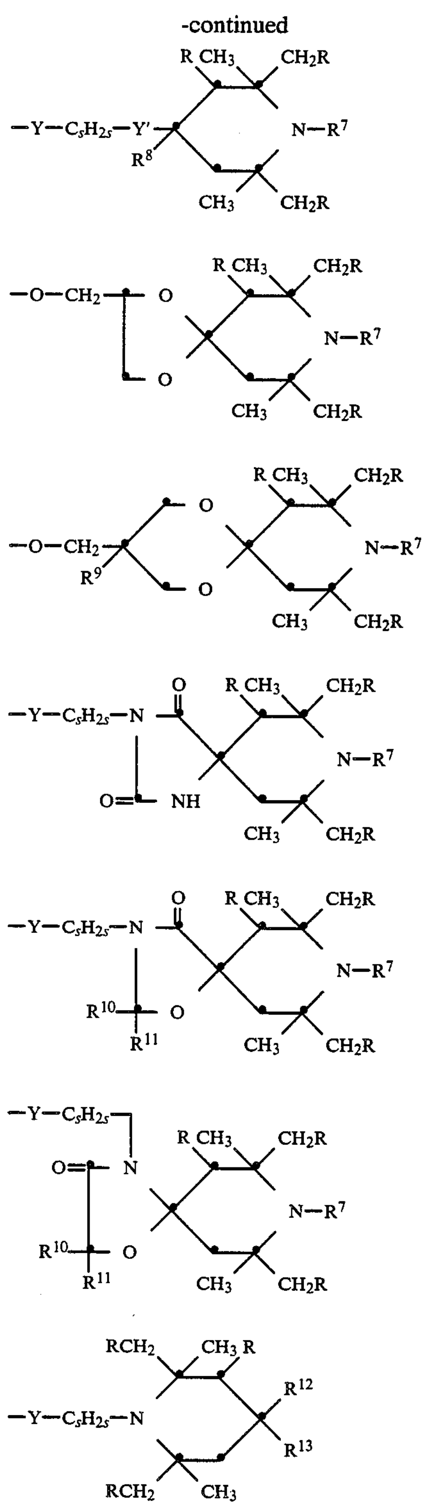

in which Y and Y', independently of each other, are each —O— or —N($R^6$)—, $R^6$ is hydrogen, $C_1$-$C_{18}$-alkyl, $C_3$-$C_6$-alkenyl, $C_5$-$C_{12}$-cycloalkyl, $C_7$-$C_{12}$-phenylalkyl, $C_3$-$C_{12}$-alkoxyalkyl, $C_4$-$C_{12}$-dialkylaminoalkyl, a group of the formula —$C_sH_{2s}$—X'—CO—$R^{14}$ or

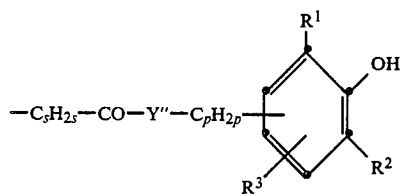

or a group of the formula XVI

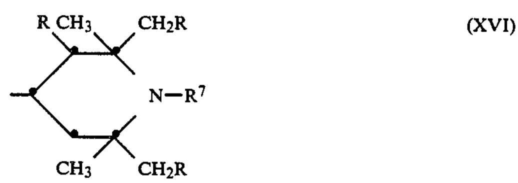

R is hydrogen, or methyl, $R^7$ is hydroxyl, $C_1$-$C_{12}$-alkyl, $C_3$-$C_6$-alkenyl, $C_3$-$C_4$-alkynyl, $C_7$-$C_{12}$-phenylalkyl, glycidyl, $C_1$-$C_4$-alkyl which is substituted by halogen, —CN, —COOR$^{15}$ or —CON($R^{16}$)($R^{17}$), a group of the formula —CO—$R^{14}$, —CO—OR$^{15}$, —CO—N($R^{16}$)($R^{17}$), —$CH_2$—CH($R^{18}$)—OR$^{19}$, —SO—$R^{20}$, —$SO_2$—$R^{20}$, —OR$^{15}$ or —OOC—$R^{14}$, $R^8$ is hydrogen, —CN, —COOR$^{15}$, $CONH_2$ or —CON($R^{16}$)($R^{17}$), $R^9$ is methyl or ethyl, $R^{10}$ is hydrogen, $C_1$—$C_{12}$-alkyl, $C_5$—$C_8$-cycloalkyl or benzyl, and $R^{11}$ is $C_1$-$C_{12}$-alkyl, $C_5$-$C_8$-cycloalkyl or phenyl, or $R^{10}$ and $R^{11}$, together with the C atom to which they are bonded, are a $C_5$—$C_{12}$-cycloalkane or alkylcycloalkane ring, $R^{12}$ is hydrogen, —OR$^{21}$, —OOC—$R^{14}$ or —N($R^{22}$)—CO—$R^{14}$, and $R^{13}$ is hydrogen, —CN, —COOR$^{15}$, —$CONH_2$ or —CON($R^{16}$)($R^{17}$), or $R^{12}$ and $R^{13}$ are together a group of the formulae

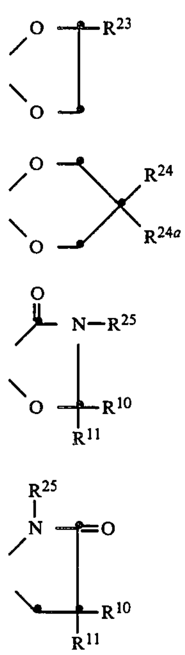

-continued

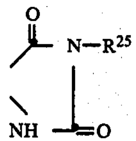

q is 1 or 2, s is an integer from 2-6, Y'' is —O— or —$NR^{5a}$—, in which $R^{5a}$ is defined in the same way as $R^5$ or is a group of the formula XVI, $R^{14}$ is hydrogen, $C_1$-$C_{12}$-alkyl, $C_2$-$C_6$-alkenyl, chloromethyl, $C_5$-$C_{12}$-cycloalkyl, $C_7$-$C_{12}$-phenylalkyl, phenyl, $C_7$-$C_{10}$-alkylphenyl or such phenyl, phenylmethyl or phenylethyl as is substituted by 1 or 2 $C_1$-$C_4$-alkyl groups and a hydroxyl group, $R^{15}$ is $C_1$-$C_{12}$-alkyl, allyl, benzyl or cyclohexyl, $R^{16}$ is $C_1$-$C_{12}$-alkyl, allyl, cyclohexyl, benzyl or phenyl, and $R^{17}$ is hydrogen, $C_1$-$C_8$-alkyl or allyl, or $R^{16}$ and $R^{17}$, together with the N atom, are a 5- or 6-membered heterocyclic ring, $R^{18}$ is hydrogen, $C_1$-$C_4$-alkyl, $C_2 \propto C_{13}$-alkoxymethyl, phenyl or phenoxymethyl, $R^{19}$ is hydrogen, $C_1$-$C_{12}$-alkyl, —CO—$R^{14}$ or —CO—N($R^{16}$)($R^{17}$), $R^{20}$ is $C_1$-$C_{12}$-alkyl, phenyl or $C_7$-$C_{22}$-alkylaryl, $R^{21}$ is hydrogen, $C_1$-$C_{12}$-alkyl, allyl or benzyl, $R^{22}$ is hydrogen, $C_1$-$C_{12}$-alkyl, $C_5$-$C_{12}$-cycloalkyl or benzyl, $R^{23}$ is hydrogen, methyl or ethyl, $R^{24}$ and $R^{24a}$, independently of each other, are each H or $C_1$-$C_4$-alkyl, and $R^{25}$ is hydrogen, C-$C_{12}$-alkyl, $C_3$-$C_{12}$-alkoxyalkyl, $C_5$-$C_{12}$-cycloalkyl, allyl or benzyl, or (c) a group of the formula —$OR^{26}$, —$SR^{27}$, —P(O)($OR^{28}$)$_2$ or —N($R^{29}$)($R^{30}$), in which $R^{26}$ is hydrogen, $C_1$-$C_{18}$-alkyl, $C_3$-$C_6$-alkenyl, $C_3$-$C_{12}$-alkoxyalkyl, $C_4$-$C_{12}$-dialkylaminoalkyl, phenyl, $C_7$-$C_{22}$-alkylaryl, $C_7$-$C_9$-phenylalkyl or $C_5$-$C_{12}$-cycloalkyl, $R^{27}$ is $C_1$-$C_{18}$-alkyl, $C_5$-$C_{12}$-cycloalkyl, phenyl, $C_7$-$C_{12}$-alkylphenyl, $C_7$-$C_9$-phenylalkyl, —$CH_2COOR^{31}$ or —$CH_2CH_2COOR^{31}$, $R^{31}$ is hydrogen or $C_1$-$C_{12}$-alkyl, $R^{28}$ is $C_1$-$C_{12}$-alkyl, phenyl, tolyl, benzyl or a group of the formula XVI, $R^{29}$ and $R^{30}$, independently of each other, are each hydrogen, $C_1$-$C_{12}$-alkyl, $C_2$-$C_4$-alkyl which is substituted by $C_1$-$C_4$-alkoxy, $R^{14}$—COO— or $C_2$-$C_8$- dialkylamino, $C_5$-$C_{12}$-cycloalkyl, $C_3$-$C_6$-alkenyl or $C_7$-$C_9$-phenylalkyl, or $R^{29}$ and $R^{30}$, together with the N atom to which they are bonded, are a 5- or 6-membered heterocyclic ring, and $R^{III}$ can also be a group of the formula XVII

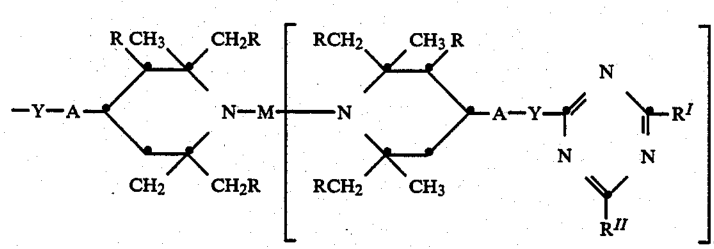

(XVII)

in which t is 1, 2 or 3, A is a direct bond, a —($CH_2$)$_q$—group or a —Y'—$C_sH_{2s}$—group, and M, if t=1, is a divalent group, $C_2$-$C_{12}$-alkylene, $C_4$-$C_8$-alkenylene, xylylene or a radical of the formula —$CH_2$—C≡C—$CH_2$—

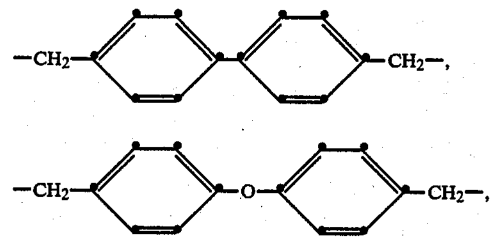

—$CH_2$—COO—B—OOC—$CH_2$—, —$CH_2$—CH(OH)—$CH_2$—, —$CH_2$CH(OH)$CH_2$—D—$CH_2$CH(OH)$CH_2$—, —$CH_2$—CH($R^{18}$)—OOC—$R^{33}$—COO—CH($R^{18}$)—$CH_2$— or —CO—NH—G—NH—CO—, in which B is $C_2$-$C_{12}$-alkylene, $C_4$-$C_8$-oxaalkylene or cyclohexylene, D is a divalent radical of the formula —O—$R^{32}$—O— or —OOC—$R^{33}$—COO—, in which $R^{32}$ is $C_2$-$C_{12}$-alkylene, $C_6$-$C_{12}$-cycloalkylene, $C_6$-$C_{12}$-arylene or -phenylene-Z-phenylene, and Z is —O—, —$CH_2$—, >C($CH_3$)$_2$ or —$SO_2$, $R^{33}$ is a direct bond, $C_1$-$C_{12}$-alkylene, $C_2$-$C_6$-alkenylene, $C_6$-$C_{12}$-cycloalkylene or cycloalkenylene or $C_6$-$C_{12}$-arylene, and G is a divalent aliphatic, cycloaliphatic, aromatic or aromatic-aliphatic radical having 6-15 C atoms, M, if t=2, is a trivalent radical of the formula

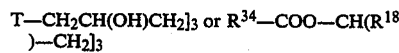

T—$CH_2CH(OH)CH_2]_3$ or $R^{34}$—COO—CH($R^{18}$)—$CH_2]_3$ in which T is a trivalent radical of the formulae

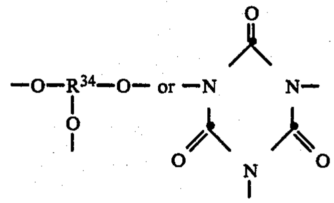

and $R^{34}$ is a trivalent aliphatic hydrocarbon radical having 3-10 carbon atoms or a trivalent aromatic hydrocarbon radical having 6-10 C atoms, and M, if t=3, is a tetravalent radical of the formula Q—$CH_2CH(OH)CH_2]_4$ or $R^{35}$—COO—CH($R^{18}$)—$CH_2]_4$ in which Q is a group of the formula

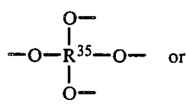

or

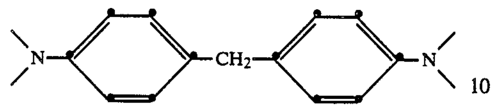

and $R^{35}$ is a tetravalent aliphatic hydrocarbon radical having 4–10 C atoms or a tetravalent aromatic hydrocarbon radical having 6–12 C atoms, $R^{IV}$ is the m-valent radical of a polyamine or of a polyol, and m is an integer from 2 to 6, $R^{V}$ is a divalent group of the formula —Y—$R^{36}$—Y— or

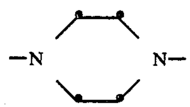

in which $R^{36}$ is $C_2$-$C_{12}$-alkylene, $C_5$-$C_{12}$-cycloalkylene, $C_8$-$C_{12}$-aralkylene, $C_6$-$C_{12}$-arylene, $C_4$-$C_8$-alkylene which is interrupted by O or $NR^5$ or a group of the formula

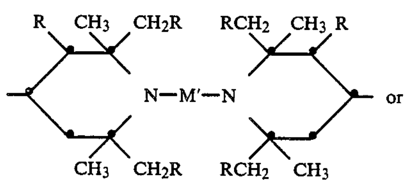

or

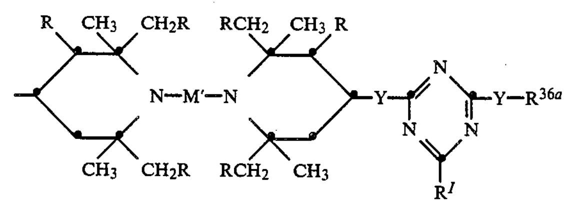

in which M' is a divalent group of the formula M, and $R^{36a}$ is $C_2$-$C_{12}$-alkylene, $C_5$-$C_{12}$-cycloalkylene, $C_8$-$C_{12}$-aralkylene, $C_6$-$C_{12}$-arylene or $C_4$-$C_8$-alkylene which is interrupted by O or $NR^5$, n is 2 to 50, and E and E' are each terminal groups, and at least one of the radicals $R^I$, $R^{II}$ and $R^{III}$ contains a sterically hindered phenol group and at least one of the radicals $R^I$, $R^{II}$, $R^{III}$, $R^{IV}$ and $R^{V}$ contains a polyalkylpiperidine radical.

3. A colour-photographic recording material according to claim 2, which contains, as a stabiliser, a compound which is of the formula I, II or III and which contains in its molecule at least one sterically hindered phenol group and at least one N-substituted 2,2,6,6-tetramethylpiperidine group.

4. A colour-photographic recording material according to claim 2, which contains, as a stabiliser, a compound of the formula I in which $R^I$, $R^{II}$ and $R^{III}$, independently of one another, are each (a) a group of the formula IVa

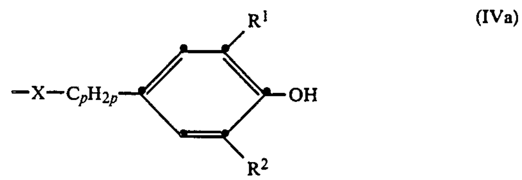

(IVa)

in which p is an integer from 1 to 4, and X, $R^1$ and $R^2$ are as defined in claim 2, (b) a group of the formulae VIIa or XVa

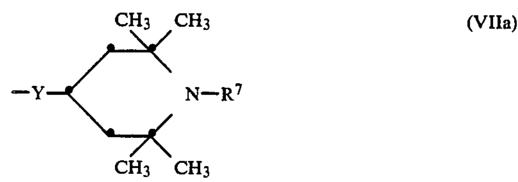

(VIIa)

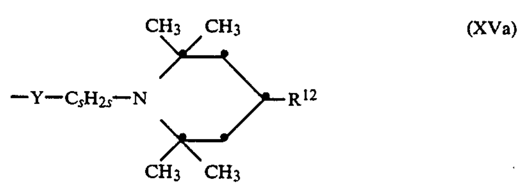

(XVa)

in which Y is —O— or —$NR^6$—, and $R^6$, $R^7$, $R^{12}$ and s are as defined in claim 2, or (c) a group of the formula —$OR^{26}$, —$SR^{27}$, —P(O)$(OR^{28})_2$ or —N($R^{29}$) ($R^{30}$), in which $R^{26}$, $R^{27}$, $R^{28}$, $R^{29}$ and $R^{30}$ are as defined in claim 2, and at least one of the radicals $R^I$, $R^{II}$ and $R^{III}$ contains a sterically hindered phenol group, and at least one of the radicals $R^I$, $R^{II}$ and $R^{III}$ contains an N-substituted 2,2,6,6-tetramethylpiperidine group.

5. A colour-photographic recording material according to claim 4, which contains, as a stabiliser, a compound of the formula I in which $R^I$, $R^{II}$ and $R^{III}$, independently of one another, are each (a) a group of the formula IVa in which $R^1$ is hydrogen or $C_1$-$C_4$-alkyl, $R^2$ is $C_1$-$C_4$-alkyl, and X and p are as defined in claim 4, or (b) a group of the formula VIIa or XVa in which Y is —O— or —$NR^6$—, $R^6$ is hydrogen, $C_1$-$C_8$-alkyl, allyl, cyclohexyl, benzyl or a group of the formula —$C_sH_{2s}$—X'—CO—$R^{14}$ in which s=2 or 3, X' is —O— and $R^{14}$ is such phenyl, phenylmethyl or phenylethyl as is substituted by 1 or 2 $C_1$-$C_4$-alkyl groups and a hydroxyl group, $R^7$ is methyl, allyl, benzyl, 2-hydroxyethyl, acetyl, acryloyl or a group of the formula —CON($R^{16}$)($R^{17}$) in which $R^{16}$ is $C_1$-$C_8$-alkyl, cyclohexyl or phenyl, and $R^{17}$ is hydrogen or $C_1$-$C_8$-alkyl, and $R^{12}$ is hydrogen, or (c) a group of the formula —$OR^{26}$, —$SR^{27}$ or —N($R^{29}$)($R^{30}$) in which $R^{26}$ is $C_1$-$C_{12}$-alkyl, phenyl, $C_7$-$C_{22}$-alkylaryl, benzyl or cyclohexyl, $R^{27}$ is $C_1$-$C_{12}$-alkyl, cyclohexyl, phenyl, —$CH_2COO$($C_1$-$C_{12}$-alkyl) or —$CH_2CH_2COO$($C_1$-$C_{12}$-alkyl), and $R^{29}$ and $R^{30}$ are each hydrogen, $C_1$-$C_{12}$-alkyl, benzyl or allyl.

6. A colour-photographic recording material according to claim 2, which contains, as a stabiliser, a compound of the formula II in which m=2 and $R^{IV}$ is a divalent group of the formula

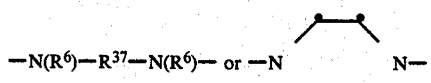

in which $R^{37}$ is $C_2$–$C_{12}$-alkylene, $C_4$–$C_8$-alkylene which is interrupted by —O— or —$NR^5$—, $C_6$–$C_{15}$-arylene, $C_8$–$C_{12}$-aralkylene or $C_5$–$C_{12}$-cycloalkylene, and $R^5$ and $R^6$ are as defined in claim 2.

7. A colour-photographic recording material according to claim 2, which contains, as a stabiliser, a compound of the formula II in which m=3 and $R^{IV}$ is a trivalent group of the formula $$—N(R^6)—(CH_2)_a—\overset{|}{N}(R^6)—(CH_2)_a—N(R^6)—$$

or m=4 and $R^{IV}$ is a tetravalent group of the formula

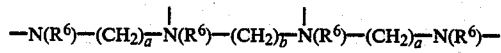

in which a is 2 or 3, b is 2–12, and $R^6$ is as defined in claim 2.

8. A colour-photographic recording material according to claim 2, which contains, as a stabiliser, a compound of the formula III in which $R^V$ is a divalent group of the formula —$N(R^6)$—$R^{36a}$—$N(R^6)$— in which $R^{36a}$ and $R^6$ are as defined in claim 2.

9. A colour-photographic recording material according to claim 8, wherein, in the compound of the formula III, the terminal group E is hydrogen and the terminal group E' is a group of the formula —$N(R^6)$—$R^{36a}$—$NHR^6$.

10. A colour-photographic recording material according to claim 8, which contains, as a stabiliser, a compound of the formula III in which $R^I$ is a group of the formula

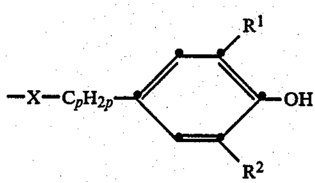

and $R^V$ is a group of the formula

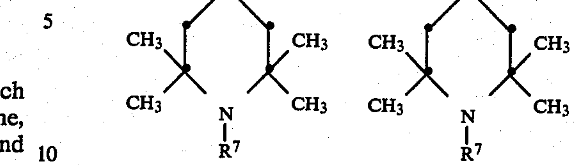

in which w is 2–6.

11. A colour-photographic recording material according to claim 10, which contains, as a stabiliser, a compound of the formula III in which $R^I$ is a group of the formula

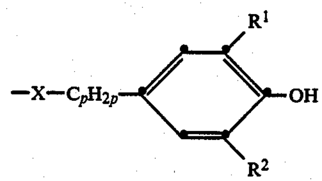

and $R^V$ is a group of the formula

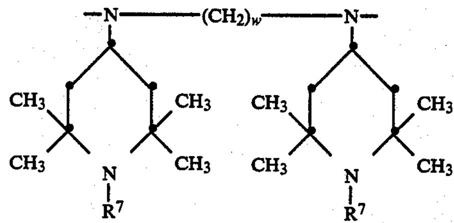

in which p is 1–4, X is —O—, —S—, —NH— or —N($C_1$–$C_4$-alkyl)-, $R^1$ is hydrogen or $C_1$–$C_4$-alkyl, $R^2$ is $C_1$–$C_4$-alkyl, w is 2–6 and $R^7$ is methyl, allyl, benzyl, 2-hydroxyethyl, acetyl, aryloyl or a group of the formula —$CON(R^{16})(R^{17})$ in which $R^{16}$ is $C_1$–$C_8$-alkyl, cyclohexyl or phenyl and $R^{17}$ is hydrogen or $C_1$–$C_8$-alkyl.

12. A colour-photographic recording material according to claim 1, which, in addition to a stabiliser of the formula I, II or III, contains an optical stabiliser from the class of the ultraviolet absorbers.

13. A colour-photographic recording material according to claim 1, which contains 1 to 2,000 mg of compound of the formula I, II or III per $m^2$.

* * * * *